(12) United States Patent
Danielsson et al.

(10) Patent No.: US 10,575,801 B2
(45) Date of Patent: *Mar. 3, 2020

(54) PHOTON COUNTING DETECTOR

(71) Applicant: Prismatic Sensors AB, Stockholm (SE)

(72) Inventors: Mats Danielsson, Täby (SE); Staffan Karlsson, Bromma (SE); Xuejin Liu, Täby (SE); Martin Sjölin, Stockholm (SE); Anders Björklid, Ljungsbro (SE); Torbjörn Hjärn, Vaxholm (SE)

(73) Assignee: PRISMATIC SENSORS AB, Stockholm (SE)

( * ) Notice: Subject to any disclaimer, the term of this patent is extended or adjusted under 35 U.S.C. 154(b) by 101 days.

This patent is subject to a terminal disclaimer.

(21) Appl. No.: 15/617,994

(22) Filed: Jun. 8, 2017

(65) Prior Publication Data

US 2018/0042562 A1 Feb. 15, 2018

Related U.S. Application Data

(63) Continuation-in-part of application No. 15/594,879, filed on May 15, 2017, now Pat. No. 10,048,390, and a continuation-in-part of application No. 15/484,705, filed on Apr. 11, 2017, now Pat. No. 10,379,233, and
(Continued)

(51) Int. Cl.
*A61B 6/00* (2006.01)
*A61B 6/03* (2006.01)

(52) U.S. Cl.
CPC ............ *A61B 6/4241* (2013.01); *A61B 6/032* (2013.01)

(58) Field of Classification Search
CPC .......... A61B 6/4241; A61B 6/032; A61B 6/54
See application file for complete search history.

(56) References Cited

U.S. PATENT DOCUMENTS

| 5,693,948 | A | 12/1997 | Sayed et al. | |
|---|---|---|---|---|
| 6,573,762 | B1 * | 6/2003 | Wessendorf | G06G 7/161 250/370.01 |
| 6,931,092 | B2 | 8/2005 | Joshi et al. | |

(Continued)

FOREIGN PATENT DOCUMENTS

| EP | 3049829 B1 | 3/2017 | |
|---|---|---|---|
| JP | 2013170922 A | 9/2013 | |
| WO | WO-2017033675 A1 * | 3/2017 | ............... G01T 1/17 |

OTHER PUBLICATIONS

Sep. 19, 2017, International Search Report issued for related International Application No. PCT/SE2017/050780.
(Continued)

*Primary Examiner* — David P Porta
*Assistant Examiner* — Jeremy S Valentiner
(74) *Attorney, Agent, or Firm* — Young & Thompson

(57) ABSTRACT

A photon-counting detector includes a first subset of detector modules and at least one second subset of detector modules. Each detector module has power-consuming circuitry. Power-consuming circuitry of detector modules in the first subset is configured, in an operational mode in which the detector modules are powered on, to consume a first amount of power. Correspondingly, power-consuming circuitry of detector modules in the at least one second subset is configured, in the operational mode, to consume a second amount of power that is lower than the first amount of power.

27 Claims, 12 Drawing Sheets

Related U.S. Application Data a continuation of application No. PCT/SE2017/050497, filed on May 15, 2017.

(60) Provisional application No. 62/373,413, filed on Aug. 11, 2016.

(56) References Cited

U.S. PATENT DOCUMENTS

| | | | |
|---|---|---|---|
| 7,065,173 B2 | 6/2006 | Lacey et al. | |
| 7,236,562 B2 | 6/2007 | Joshi et al. | |
| 7,381,964 B1 | 6/2008 | Kump et al. | |
| 8,476,594 B2 | 7/2013 | Frach et al. | |
| 8,779,907 B2 | 7/2014 | Liu et al. | |
| 9,086,360 B2 | 7/2015 | Joshi et al. | |
| 9,223,038 B2 | 12/2015 | Hannemann et al. | |
| 2004/0239377 A1* | 12/2004 | Turner | G01T 1/17 327/94 |
| 2007/0114424 A1* | 5/2007 | Danielsson | A61B 6/4241 250/370.09 |
| 2008/0099689 A1 | 5/2008 | Nygard et al. | |
| 2008/0203309 A1* | 8/2008 | Frach | G01T 1/1642 250/362 |
| 2009/0164807 A1* | 6/2009 | Chi | G06F 1/26 713/300 |
| 2010/0204942 A1* | 8/2010 | Danielsson | G01T 1/242 702/85 |
| 2010/0215142 A1* | 8/2010 | Dafni | A61B 6/032 378/19 |
| 2014/0348290 A1 | 11/2014 | Harrison et al. | |
| 2015/0312999 A1 | 10/2015 | Takahashi et al. | |
| 2015/0313565 A1* | 11/2015 | Matsuda | A61B 6/032 378/19 |
| 2016/0011323 A1 | 1/2016 | Sasaki et al. | |
| 2016/0174920 A1 | 6/2016 | Lacey et al. | |
| 2016/0302302 A1* | 10/2016 | Yachi | H05K 1/0216 |
| 2016/0324494 A1 | 11/2016 | Roessl et al. | |
| 2018/0203133 A1* | 7/2018 | Farsoni | G01T 1/17 |
| 2018/0206805 A1* | 7/2018 | Onouchi | G01T 1/17 |

OTHER PUBLICATIONS

Alvarez and Macovski. Energy-selective reconstructions in X-ray computerised tomography. Phys. Med. Biol., 21 (5):733, 1976.

Roessl and Proksa. K-edge imaging in X-ray computed tomography using multi-bin photon counting detectors. Phys. Med. Biol., 52(15):4679, 2007.

Liu, Grönberg, Sjölin, Karlsson and Danielsson, "Count rate performance of a silicon-strip detector for photon-counting spectral CT", Nucl. Instr. and Meth. A, vol. 827, p. 102-106. 2016.

Gustavsson, Amin, Bjorklid, Ehliar, Xu and Svensson. A high-rate energy-resolving photon-counting ASIC for spectral computed tomography. IEEE Transactions on Nuclear Science, 59(1), 30-39, 2012.

Bornefalk, Persson, Xu, Karlsson, Svensson and Danielsson, "Effect of Temperature Variation on the Energy Response of a Photon Counting Silicon CT Detector", IEEE Transactions on Nuclear Science, 60 (2):1442-1449, 2013.

* cited by examiner

PHOTON COUNTING DETECTOR

TECHNICAL FIELD

The present embodiments generally relate to photon-counting detectors and X-ray detector systems comprising such photon-counting detectors, and in particular to photon-counting detectors with reduced power consumption.

BACKGROUND

A modern clinical Computed Tomography (CT) system consists in short of a fan-beam geometry with an X-ray source or tube facing an arc-shaped detector. An acquisition of a large number of X-ray projections at different angles around a patient is performed by rotating the source and the detector continuously over 360 degrees within sub-seconds. Both the attenuated (after the patient) and the unattenuated (before the patient) X-ray intensities are recorded, from which a 3D spatial distribution of the linear attenuation coefficients within the patient is reconstructed, accurately delineating organs and tissues.

The detector is one of the most important components of a CT system. Scintillation detectors, which consist of scintillators coupled to photodiodes, are most frequently used in modern CT systems. In these detectors, an interacting X-ray photon is first converted to scintillation lights in the scintillators. Electron-hole pairs are generated through the absorption of scintillation lights in photodiodes. The energy deposited by the interacting photons over a certain exposure time is integrated to obtain electrical signals output by the photodiodes that are proportional to the total deposited energy. In this way, the electronic noise produced by detector elements in the detector and readout electronics is also integrated into the output signals that are transmitted to the data processing system via analog to digital converting application-specific integrated circuits (ASICs) for image reconstruction.

Components within the energy-integrating detector, such as scintillation detector, are very temperature sensitive, in particular the photodiodes. For instance, if the photodiodes are made of silicon, the dark current from the bulk silicon, which is a major source of the electronic noise, will be doubled for every 8° C. temperature increase. It is, thus, desirable to maintain the energy-integrating detector at a controlled temperature both during its operation and system calibration to avoid image quality issues that may be caused by temperature drifts in the detector components.

Methods and devices for thermal control in a modern CT detector typically employ coolers and/or heaters to provide a constant temperature environment while the detector electronics are turned on continuously [1-4]. A typical operating temperature for an energy-integrating detector is higher than 36° C. [5] with its allowance for variation less than 0.5° C.

Photon-counting detectors that may be used in the next generation X-ray and CT imaging systems work in a totally different way as compared to the energy-integrating detectors. Incident X-ray photons are directly transferred to electrical pulses with pulse amplitudes proportional to the photon energies. These electrical pulses are then fed into the corresponding ASIC channels. Each ASIC channel typically contains a charge sensitive amplifier (CSA), a pulse shaper, a number of pulse-height comparators and counters. After being amplified and shaped, each electrical pulse is compared to a number of programmable thresholds and classified according to its pulse height, and the corresponding counter is incremented.

Compared to the energy-integrating detectors, photon-counting detectors have the following advantages. Firstly, electronic noise that is integrated into the signal by the energy-integrating detectors can be rejected by setting the lowest energy threshold above the noise floor in the photon-counting detectors. Secondly, material decomposition, by which different components in the examined patient can be identified and quantified, is ready to be implemented by using the energy information extracted by the detector [6]. Thirdly, more than two basis materials can be used which benefits decomposition techniques, such as K-edge imaging whereby distribution of contrast agents, e.g., iodine or gadolinium, are quantitatively determined [7]. Last but not least, higher spatial resolution can be achieved by using smaller pixel size. Compared to the typical pixel size of 1 $mm^2$ of current energy-integrating detectors, photon-counting detectors usually use sub-square-millimeter pixel size. For instance, a silicon-strip photon-counting detector can hold a pixel size of 0.2 $mm^2$ [8].

The most promising materials for photon-counting X-ray detectors are cadmium telluride (CdTe), cadmium zinc telluride (CZT) and silicon. CdTe and CZT are employed in several photon-counting spectral CT projects for the high absorption efficiency of high-energy X-rays used in clinical CT. However, these projects are slowly progressing due to several drawbacks of CdTe/CZT. CdTe/CZT have low charge carrier mobility, which causes severe pulse pileup at flux rates ten times lower than those encountered in clinical practice. One way to alleviate this problem is to decrease the pixel size, whereas it leads to increased spectrum distortion as a result of charge sharing and K-escape. Also, CdTe/CZT suffer from charge trapping, which would lead to polarization that causes a rapid drop of the output count rate when the photon flux reaches above a certain level.

In contrast, silicon has higher charge carrier mobility and is free from the problem of polarization. The mature manufacturing process and comparably low cost are also its advantages. But silicon has limitations that CdTe/CZT does not have. Silicon sensors must be very thick to compensate for its low stopping power. Typically, a silicon sensor needs a thickness of several centimeters to absorb most of the incident photons, whereas CdTe/CZT needs only several millimeters. On the other hand, the long attenuation path of silicon also makes it possible to divide the detector into different depth segments that are read out individually. This in turn increases the detection efficiency and makes a silicon-based photon-counting detector possible to properly handle the high fluxes in CT.

However, the employment of detector elements in depth segments also brings problems to the silicon-based photon-counting detector. A large number of ASIC channels have to be employed to process data fed from the detector elements. Each of these ASIC channels typically has a power consumption of several milliwatts [9]. A full photon-counting detector with a total area larger than 200 $cm^2$ can consist of millions of such ASIC channels, which means that the total power consumption of the ASICs is on the level of thousands of watts. Consequently, silicon-based photon-counting detectors impose a challenge for the thermal management system since a lot of heat is generated by the photon-counting detector and has to be transported away, for example by water-cooling or advanced air conditioners, which will be expensive.

The prior art thermal management systems that are committed to maintain a general constant temperature environment for an energy-integrating detector will not be suitable for a photon-counting detectors.

SUMMARY

It is a general objective to provide an improved photon-counting detector.

This and other objectives are met by embodiments as disclosed herein.

An aspect of the embodiments relates to a photon-counting detector comprising a first subset of detector modules and at least one second subset of detector modules. Each detector module has power-consuming circuitry. Power-consuming circuitry of detector modules in the first subset is configured, in an operational mode in which the detector modules are powered on, to consume a first amount of power. Correspondingly, power-consuming circuitry of detector modules in the at least one second subset is configured, in the operational mode, to consume a second amount of power that is lower than the first amount of power.

Another aspect of the embodiments relates to a method of controlling a photon-counting detector according to an embodiment. The method comprises selecting, based on a control signal, an operational mode for detector modules in at least one second subset of detector modules in the photon-counting detector comprising a first subset of detector modules and the at least one second subset of detector modules. Each detector module has power-consuming circuitry. The method also comprises controlling the detector modules in the at least one second subset to operate in the selected operational mode in which power-consuming circuitry of the detector modules in the at least one second subset is configured to consume an amount of power that is lower than an amount of power consumed by power-consuming circuitry of the detector modules in the first subset.

A further aspect of the embodiments relates to a method of controlling a photon-counting detector according to an embodiment. The method comprises selecting, based on a selection signal, detector modules of the photon-counting detector belonging to at least one second subset of detector modules and/or selecting, based on the selection signal, detector modules of the photon-counting detector belonging to a first subset of detector modules. Each detector module has power-consuming circuitry. The method also comprises controlling the detector modules in the at least one second subset to operate in an operational mode in which power-consuming circuitry of the detector modules in the at least one second subset is configured to consume an amount of power that is lower than an amount of power consumed by power-consuming circuitry of the detector modules in the first subset.

Yet another aspect of the embodiments relates to a computer program comprising instructions, which when executed by at least one processor, cause the at least one processor to select, based on a control signal, an operational mode for detector modules in at least one second subset of detector modules in a photon-counting detector comprising a first subset of detector modules and the at least one second subset of detector modules. Each detector module has power-consuming circuitry. The at least one processor is also caused to control the detector modules in the at least one second subset to operate in the selected operational mode in which power-consuming circuitry of the detector modules in the at least one second subset is configured to consume an amount of power that is lower than an amount of power consumed by power-consuming circuitry of the detector modules in the first subset.

A further aspect of the embodiments relates to a computer program comprising instructions, which when executed by at least one processor, cause the at least one processor to select, based on a selection signal, detector modules of a photon-counting detector belonging to at least one second subset of detector modules and/or select, based on the selection signal, detector modules of the photon-counting detector belonging to a first subset of detector modules. Each detector module has power-consuming circuitry. The at least one processor is also caused to control the detector modules in the at least one second subset to operate in an operational mode in which power-consuming circuitry of the detector modules in the at least one second subset is configured to consume an amount of power that is lower than an amount of power consumed by power-consuming circuitry of the detector modules in the first subset.

A related aspect of the embodiments defines a carrier comprising a computer program according to above. The carrier is one of an electronic signal, an optical signal, an electromagnetic signal, a magnetic signal, an electric signal, a radio signal, a microwave signal, or a computer-readable storage medium.

The present embodiments provide photon-counting detectors that can be operated at reduced power consumption but still provide sufficient image quality during image acquisition. This is achieved by reducing the power consumption in those parts of the photon-counting detector that contribute to less interesting image features. Accordingly, the power consumption and thereby the noise suppression can be higher at the part of the photon-counting detector that captures the most interesting image features.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 3:
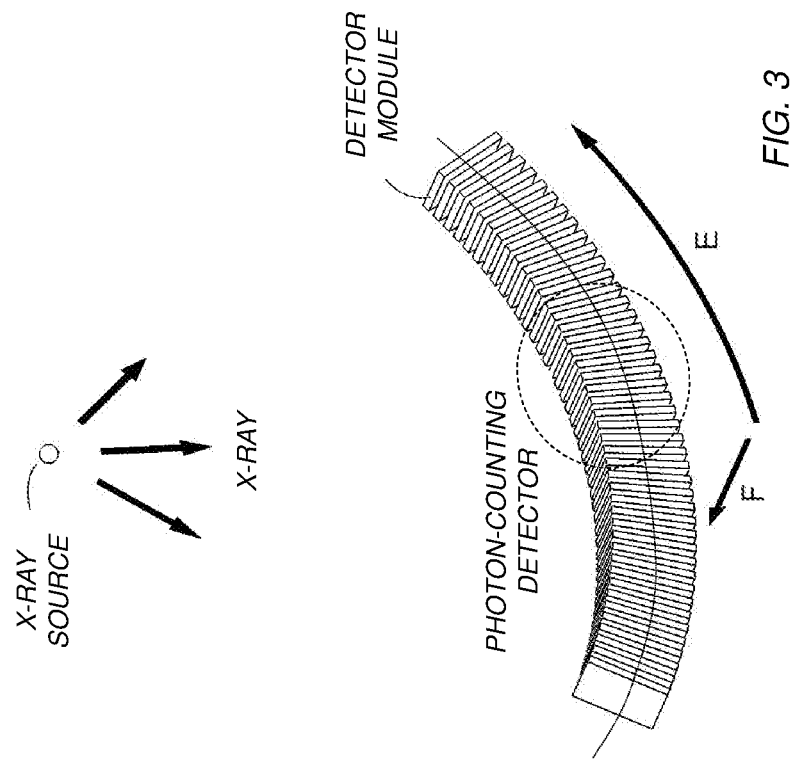
FIG. 3 is a schematic diagram of a photon-counting detector according to an embodiment.

Throughout the drawings, the same reference numbers are used for similar or corresponding elements.

The present embodiments generally relate to photon-counting detectors and X-ray detector systems comprising such photon-counting detectors, and in particular to photon-counting detectors with reduced power consumption.

Reduction of power consumption for X-ray detectors are known in the art. For instance, U.S. Pat. No. 8,779,907 discloses a portable, battery-powered digital flat panel X-ray detector that may be switched to various operational modes in order to conserve energy and extend the life of the battery. In more detail, the digital flat panel X-ray detector may be put into a sleep mode, by deactivating components that consume the majority of power while remaining components remain activated.

Such a procedure to switch the detector between sleep mode and active mode may work well for prior art digital flat panel X-ray detectors. However, such a procedure will be problematic for the next generation photon-counting detectors. For instance, a photon-counting detector utilizes calibration data, such as in the form of programmable thresholds, as a part of the photon counting. If the complete photon-counting detector is put into a sleep mode as disclosed in U.S. Pat. No. 8,779,907 then such calibration data needs to be reloaded each and every time the photon-counting detector is switched from the sleep mode into the active mode. This is a time- and processing-consuming process.

Furthermore, in the sleep mode, an X-ray detector consumes less power and thereby generates less heat. Accordingly, the temperature of the X-ray detector is typically significantly lower in the sleep mode as compared to in the active mode. However, the detection efficiency of an X-ray detector typically changes with temperature. Accordingly, some kind of temperature management system is typically implemented in the X-ray detector in order to keep the X-ray detector operating at a constant temperature. Such a thermal management system is disclosed in U.S. Pat. No. 9,223,038. In this document, photon-counting detector modules of an X-ray detector have heat-generating circuits that are controlled as a function of a power consumption of the electronics of the detector modules and the sensor material so that the total electric power of the detector modules remains constant.

This is in clear contrast to the present embodiments that relate to a photon-counting detector comprising a first subset of detector modules and at least one second subset of detector modules. Each detector module has power-consuming circuitry. According to the embodiments, power-consuming circuitry of detector modules in the first subset is configured to consume a first amount of power in an operational mode in which the detector modules are powered on. However, power-consuming circuitry of detector modules in the at least one second subset is configured to consume a second amount of power in the operational mode. This second amount of power is lower than the first amount of power.

Hence, in the operational mode in which the photon-counting detector is configured to detect incoming photons and X-rays the power-consuming circuitry of some of the detector modules, i.e., the first subset, consumes a first amount of power, whereas the power-consuming circuitry of other detector modules, i.e., the at least one second subset, consumes a second, lower amount of power. The total power consumption of the detector modules of the photon-counting detector may thereby be reduced as compared to if the power-consuming circuitry of all detector modules would have consumed the first amount of power.

The reduction in total power consumption of the photon-counting detector, however, does not require switching of all the detector modules into a sleep mode with the associated shortcoming of requiring reloading of calibration data and threshold values. In clear contrast, in the operational mode all the detector modules of the photon-counting detector are powered on but at different levels. As a consequence, there is no need to reload any calibration data for the detector modules.

Figure 1:
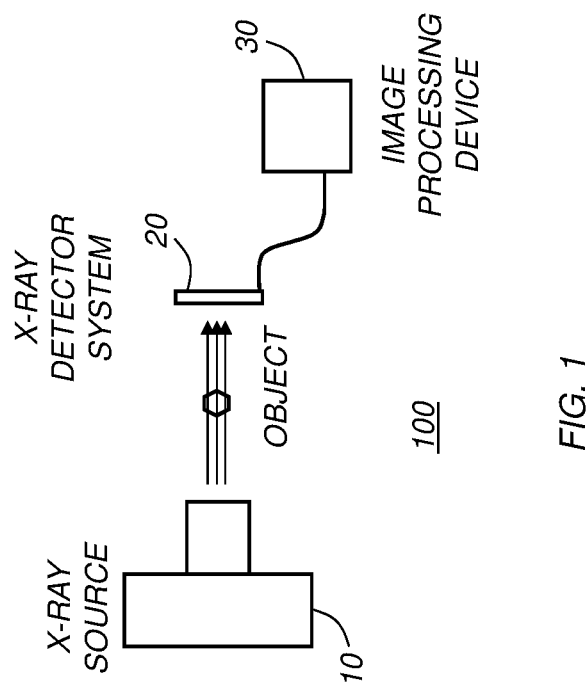
FIG. 1 is a schematic block diagram of an X-ray imaging system according to an embodiment.

It may be useful with a brief overview of an illustrative overall X-ray imaging system with reference to FIG. 1. In this illustrative but non-limiting example, the X-ray imaging system 100 basically comprises an X-ray source 10, an X-ray detector system 20 and an associated image processing device 30. In general, the X-ray detector system 20 is configured to register radiation from the X-ray source 10, which optionally has been focused by optional X-ray optics and passed an object, a subject or a part thereof. The X-ray detector system 20 is connectable to the image processing device 30 via suitable power-consuming circuitry to enable the image processing and/or image reconstruction by the image processing device 30.

Figure 2:
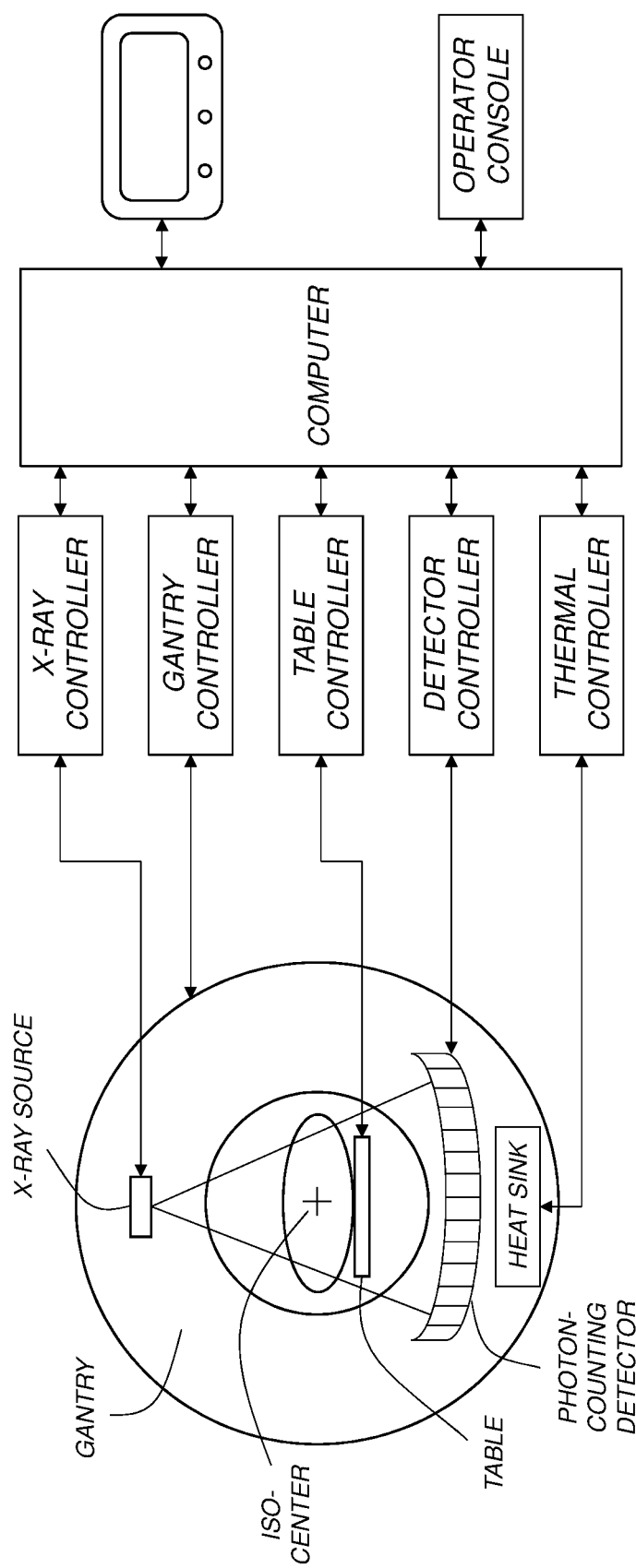
FIG. 2 is a schematic block diagram of an X-ray imaging system according to another embodiment.

FIG. 2 is a schematic block diagram of a CT system as an illustrative example of an X-ray imaging system. The CT system comprises a computer receiving commands and scanning parameters from an operator via an operator console that has a display and some form of operator interface, e.g., keyboard and mouse. The operator supplied commands and parameters are then used by the computer to provide control signals to an X-ray controller, a gantry controller and a table controller. To be specific, the X-ray controller provides power and timing signals to the X-ray source to control emission of X-rays onto the object or patient lying on the table. The gantry controller controls the rotational speed and position of the gantry comprising the X-ray source and the photon-counting detector. The table controller controls and determines the position of the patient table and the scanning coverage of the patient.

In an embodiment, the computer also performs post-processing and image reconstruction of the image data output form the photon-counting detector. The computer thereby corresponds to the image processing device as shown in FIG. 1. The associated display allows the operator to observe the reconstructed images and other data from the computer.

The X-ray source arranged in the gantry emits X-rays. An X-ray detector, in the form of a photon-counting detector, detects the X-rays after they have passed through the patient. The photon-counting detector is formed by plurality of sensors, also referred to as detector elements, and the associated power-consuming circuitry, such as application specific integrated circuits (ASICs), arranged in detector modules. The ASICs typically comprise an analog processing part, which processes the raw electrical signal from the detector elements and digitizes it, and a digital processing part, which may carry out further processing operations on the measured data, such as applying corrections, storing it temporarily, or filtering, see also FIG. 9. The photon-counting detector is optionally, but preferably connected to a cooling zone or heat sink, whereby the heat generated by the ASICs can be dissipated efficiently. During a scan to acquire X-ray projection data, the gantry and the components mounted thereon rotate about an isocenter.

The X-ray detector of the embodiments is a photon-counting detector comprising multiple detector modules. FIG. 3 is a schematic diagram of a photon-counting detector according to an exemplary embodiment. In this example, there is shown a schematic view of a photon-counting detector with an X-ray source emitting X-rays. The detector modules of the photon-counting detector are preferably arranged in a slightly curved overall configuration. Two possible scanning motions E, F of the photon-counting detector are indicated. In each scanning motion, the X-ray source may be stationary or moving. In the scanning motion indicated by E the X-ray source and photon-counting detector may be rotated around an object or patient positioned in between. In the scanning motion indicated with F the photon-counting detector and the X-ray source may be translated relative to the object or the patient, or the object or patient may be moving. Also in scan motion E the object or patient may be translated during the rotation, so called spiral scanning. By way of example, for CT implementations, the X-ray source and photon-counting detector may be mounted in a gantry that rotates around the object or patient to be imaged.

Figure 4:
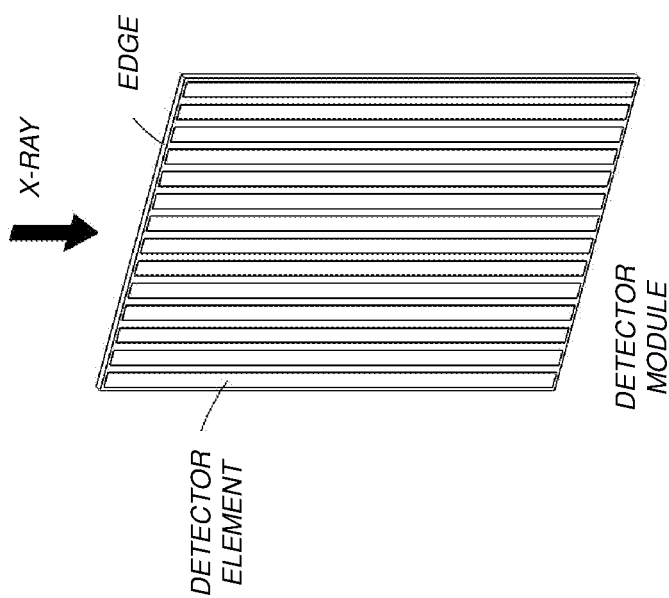
FIG. 4 is a schematic diagram of a detector module of a photon-counting detector according to an embodiment.

FIG. 4 is a schematic diagram illustrating an example of a detector module of a photon-counting detector according to an exemplary embodiment. This is an example of a semiconductor detector module with the sensor part split into detector elements in the form of strips, where each detector element is normally based on a diode. The X-rays enter through the edge of the semiconductor detector module.

Figure 5:
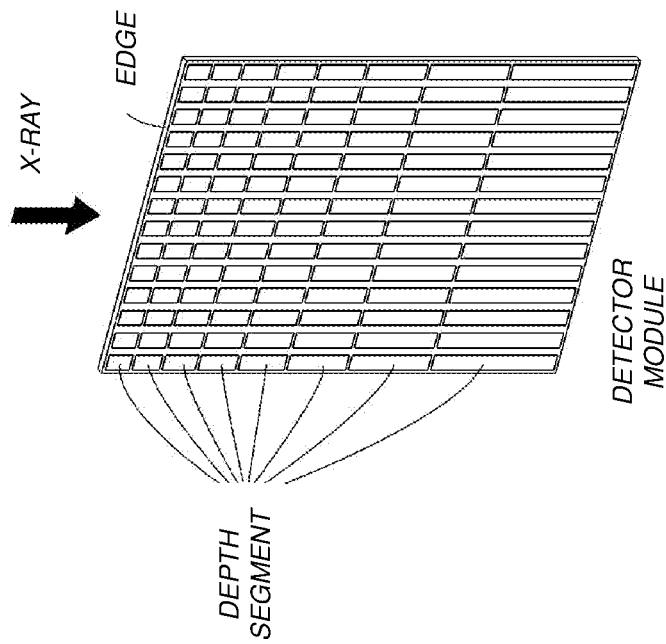
FIG. 5 is a schematic diagram of a detector module of a photon-counting detector according to another embodiment.

FIG. 5 is a schematic diagram illustrating an example of detector module according to another exemplary embodiment. In this example, the strip-based detector elements of the semiconductor detector module are split into so-called depth segments in the depth direction, again assuming the X-rays enter through the edge.

Figure 6:
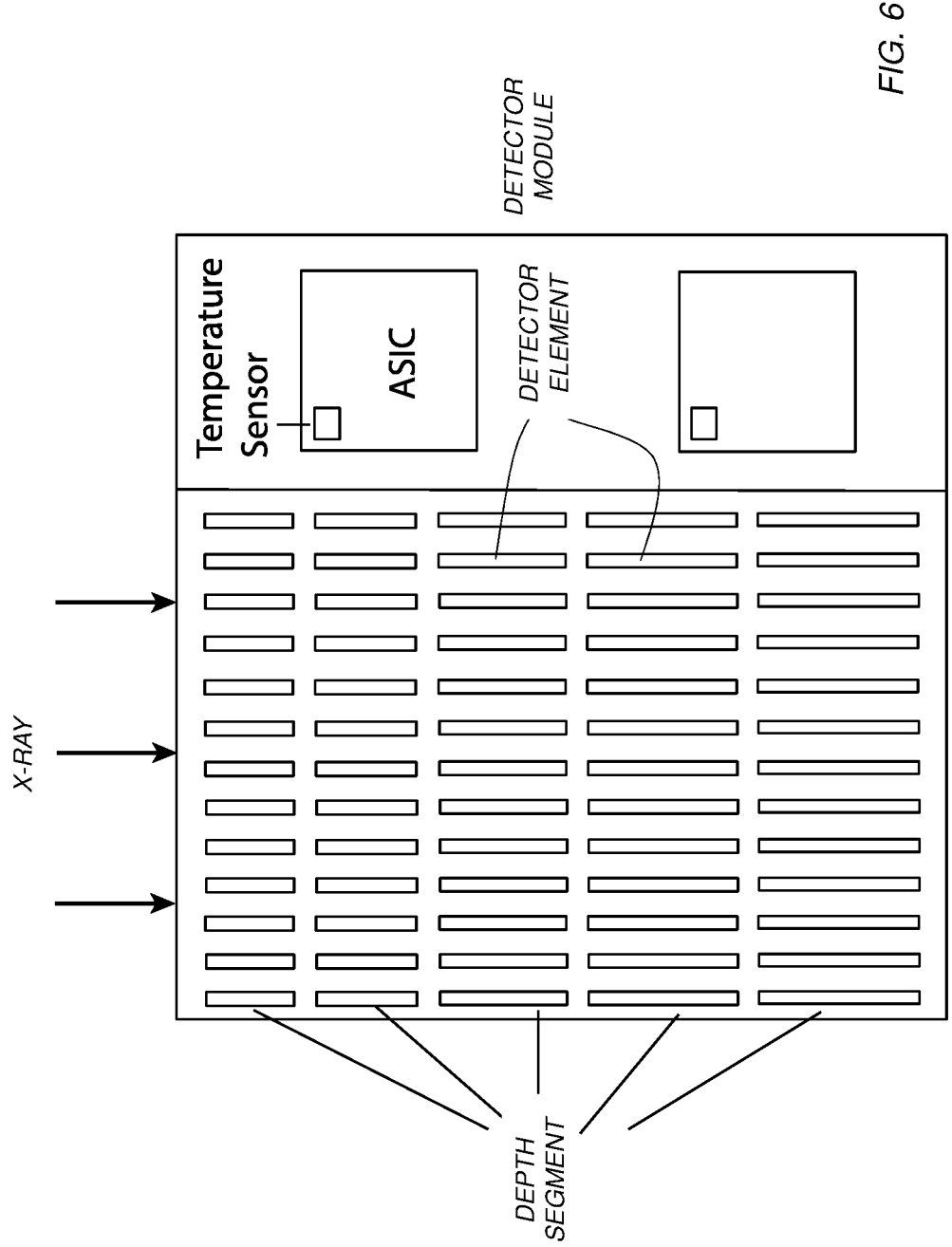
FIG. 6 is a schematic diagram of a detector module of a photon-counting detector according to a further embodiment.

The detector modules may be implemented as so-called Multi-Chip Modules (MCMs) in the sense that the detector modules have semiconductor base substrates for electric routing and for a number of ASICs, see FIG. 6. The routing will include a connection for the signal from each detector element to the ASIC input as well as connections from the ASIC to external memory and/or digital data processing (not shown). Power to the ASICs may be provided through similar routing taking into account the increase in cross-section which is required for the large currents in these connections, but the power may also be provided through a separate connection.

In an embodiment, the photon-counting detector is fabricated based on silicon as semiconductor material for the detector modules.

Hence, in an embodiment, the photon-counting detector comprises multiple semiconductor detector modules, i.e., the first subset comprises multiple semiconductor detector modules and the at least one second subset comprises multiple semiconductor detector modules. In a particular embodiment, the photon-counting detector comprises multiple silicon detector modules, i.e., the first subset comprises multiple silicon detector modules and the second subset comprises multiple silicon detector modules.

To compensate for the low stopping power of silicon, the detector modules are typically oriented in edge-on geometry with their edge directed towards the X-ray source as shown in FIGS. 4-6, thereby resulting in an absorption thickness of several centimeters. In order to cope with the high photon fluxes in clinical CT, a segmented structure of the strip-based detector elements into depth segments is preferably applied, which is achieved by implanting individual detector elements in depth segments on the silicon substrate as shown in FIGS. 5 and 6. Each individual detector element, sometimes referred to as electrode, is connected to a subsequent ASIC channel where a MCM technology is employed to integrate the ASICs and electric routing on the silicon substrate.

In an embodiment, the photon-counting detector is a photon-counting edge-on detector and each detector module has a respective edge facing incident X-rays. In a particular embodiment, a total area of the edges of the multiple detector modules is greater than 200 cm$^2$. This large total area of the edges provides a sufficient detector area for the photon-counting edge-on detector.

The employment of depth segments and individual read-out in the detector module result in a large number of ASIC channels. Moreover, a full photon-counting detector for CT applications typically has a total area greater than 200 cm$^2$, which results in a large number of detector modules, such as 1500-2000 detector modules, as schematically illustrated in FIG. 3.

As a consequence, the photon-counting detector will contain a very large number of power-consuming and thereby heat-generating ASICs, and thereby generally consume more power than the prior art flat panel CT detectors. If all detector modules of such a photon-counting detector consume maximum amount of power, e.g., the first amount of power, it will be a challenge for the thermal management system to keep the detector modules of the photon-counting detector at constant temperature and transport away the heat generated by the power-consuming ASICs in the detector modules. The present embodiments solve this problem may running or operating the power consuming circuitry of the at least one second subset in a reduced power mode as compared to the power consuming circuitry of the first subset.

In an embodiment, the first subset of detector modules is a central subset of detector modules and the at least one second subset of detector modules is at least one peripheral subset of detector modules arranged on a respective side of the central subset along an axis of the photon-counting detector, see for instance the dotted axis illustrated in FIG. 3. The power-consuming circuitry of the detector modules in the central subset is configured to consume the first amount of power in the operational mode and the power-consuming circuitry of the detector modules in the at least one peripheral subset is configured to consume the second amount of power in the operational mode.

In a particular embodiment, the photon-counting detector comprises a first peripheral subset of detector modules arranged on a first side of the central subset along the axis of the photon-counting detector and a second peripheral subset of detector modules arranged on a second, opposite side of the central subset along the axis of the photon-counting detector.

Figure 14:
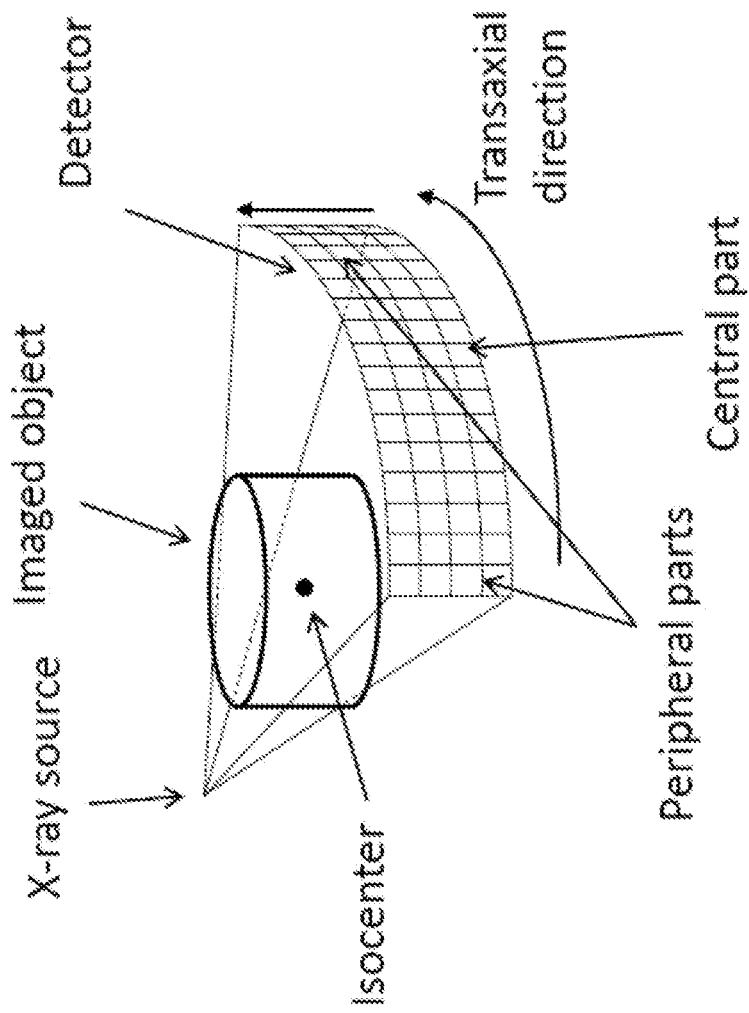
FIG. 14 is a schematic diagram illustrating an example of a configuration for CT acquisition.

This particular embodiment is schematically illustrated in FIG. 14. The figure illustrates an example of a configuration for computed tomography acquisition. Relative to the curved geometrical configuration of the photon-counting detector, the photon-counting detector can be seen as consisting of a central part or subset of detector modules and peripheral parts or subsets of detector modules along the transaxial direction or axis.

The central subset of detector modules comprises the part of the photon-counting detector that measures and detects X-rays passing close to the isocenter (center of rotation). The peripheral subsets of detector modules comprise the parts of the photon-counting detector that measure and detect X-rays passing far from the isocenter.

In computed tomography, the information value to the image for a certain X-ray incident on the photon-counting detector will be higher for X-rays incident on the detector modules in the central subset as compared to the detector modules in the peripheral subsets. This is typically true for all imaging tasks, such as the human head or heart. Accordingly, the detector modules in the peripheral subsets will only affect peripheral parts of the resulting image.

Therefore, power consumption of the photon-counting detector and thereby heat generation by the photon-counting detector can be reduced by reducing the power consumption of the detector modules in the peripheral subsets while maintaining the nominal power consumption for the detector modules in the central subset. This approach will reduce power consumption and heat generation while maintaining dose efficiency and image quality. This is possible since generally image quality and noise suppression is dependent on the power consumption of the power-consuming circuitries of the detector modules. Generally, lower power consumption correlates with more noise and lower image quality as compared to higher power consumption.

Figure 11:
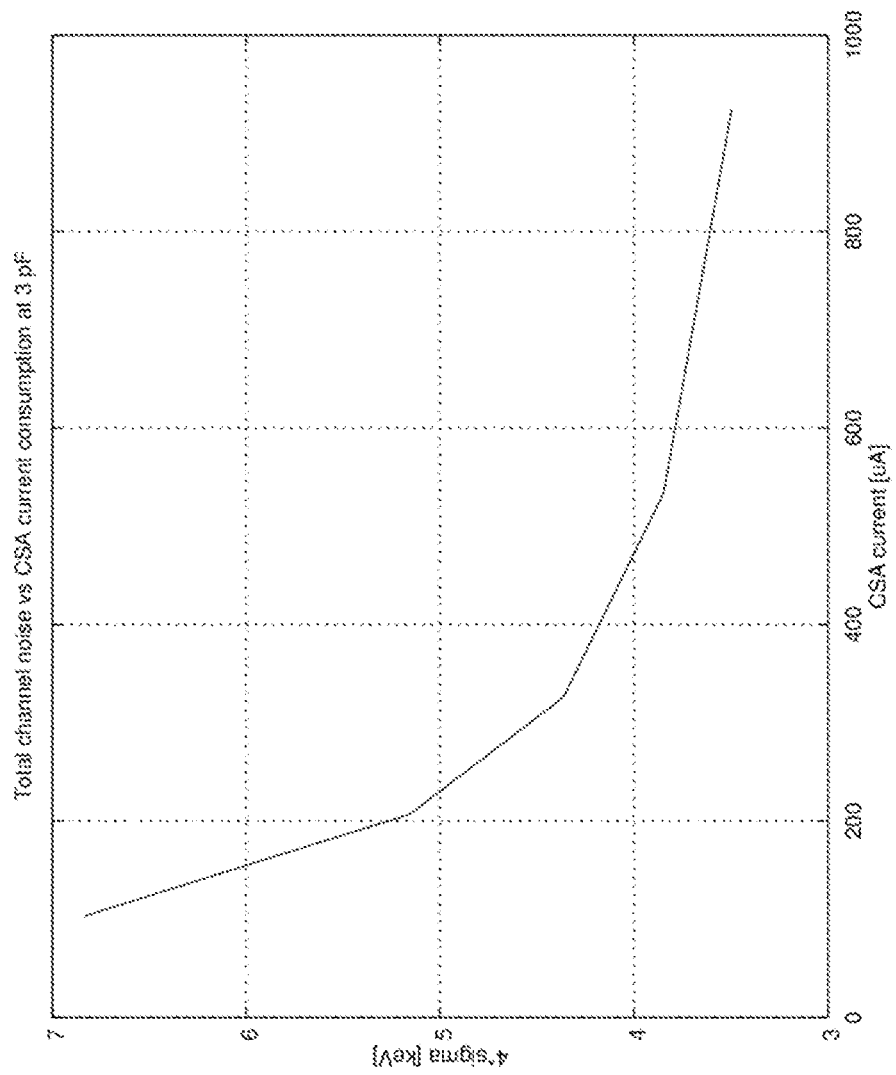
FIG. 11 is a diagram illustrating total channel noise versus charge sensitive amplifier (CSA) current consumption at 3 pF.

FIG. 11 is a diagram schematically illustrating how the total channel noise of a detector module depends on power as represented by current in a charge sensitive amplifier (CSA) at 3 pF. In a typical example, the nominal current, i.e., used for CSAs in power-consuming circuitries of the central (first) subset of detector modules, is 550 pA. When the CSA current, and thereby the power consumption, is reduced the noise increases. A typical example of the CSA current in power-consuming circuitries of the peripheral (second) subsets of detector modules is about 100-120 µA.

Thus, since the most interesting image features are often located near the isocenter, it is important to have the highest image quality in the central parts of the image. Accordingly, the CSA current, as a representation of the amount of power consumed by detector modules, should be higher in the detector modules contributing to the central parts of the image, i.e., the detector modules in the central (first) subset. The CSA current, as a representation of the amount of power consumed by detector modules, could however be lower for the detector modules that merely or mainly contribute to the peripheral, less important parts of the image, i.e., the detector modules in the peripheral (second) subsets.

In an embodiment, each power-consuming circuitry of the detector modules is a respective ASIC as shown in FIG. 6. A detector module may comprise one or multiple, i.e., at least two, ASICs as schematically shown in FIG. 6.

In an embodiment, each ASIC comprises at least one respective input channel connected to a respective detector element in the detector module. Each such input channel comprises a respective amplifier. The respective amplifier in the ASICs of the detector modules in the first (central) subset is configured to consume a third amount of power in the operational mode. Correspondingly, the respective amplifier in the ASICs of the detector modules in the at least one second (peripheral) subset is configured to consume a fourth amount of power in the operational mode. The fourth amount of power is lower than the third amount of power.

In an embodiment, each ASIC comprises at least one respective input channel connected to a respective detector element in the detector module. Each such input channel comprises a respective charge sensitive amplifier (CSA). The respective CSA in the ASICs of the detector modules in the first (central) subset has a first current consumption in the operational mode. Correspondingly, the respective CSA in the ASICs of the detector modules in the at least one second (peripheral) subset has a second current consumption in the operational mode. The second current consumption is lower than the first current consumption.

In a typical embodiment, each ASIC comprises multiple CSAs, such as several tens of CSAs and even up to more than hundreds CSAs depending on the number of detector elements present in the detector modules. In such an approach, the current to all CSAs in an ASIC could be set to a same current level or currents could be set individually or groupwise for different CSAs or groups of CSAs in an ASIC. It is also possible that the current level(s) of CSAs in one ASIC of a detector module is(are) different from the current level(s) of the CSAs in another ASIC of the same detector module. The latter approaches above generally achieve a finer control of the current consumption and thereby power consumption of the detector modules in the photon-counting detector.

Thus, in a particular embodiment, each ASIC comprises multiple input channels connected to a respective detector element in the detector module and each such input channel comprises a respective amplifier, preferably a respective CSA. A total current consumption of the respective amplifiers, preferably CSAs, in the ASICs of the detector modules in the at least one second subset is lower than a total current consumption of the respective amplifiers, preferably CSAs, in the ASICs of the detector modules in the first subset.

In an embodiment, the photon-counting detector is a so-called energy-discriminating or energy-resolving photon-counting detector, sometimes referred to as a spectral X-ray detector. In this embodiment, see FIG. 7, each registered photon generates a current pulse which is compared to a set of thresholds ($T_1$-$T_N$), thereby counting the number of photons incident in each of a number of energy bins.

Figure 7:
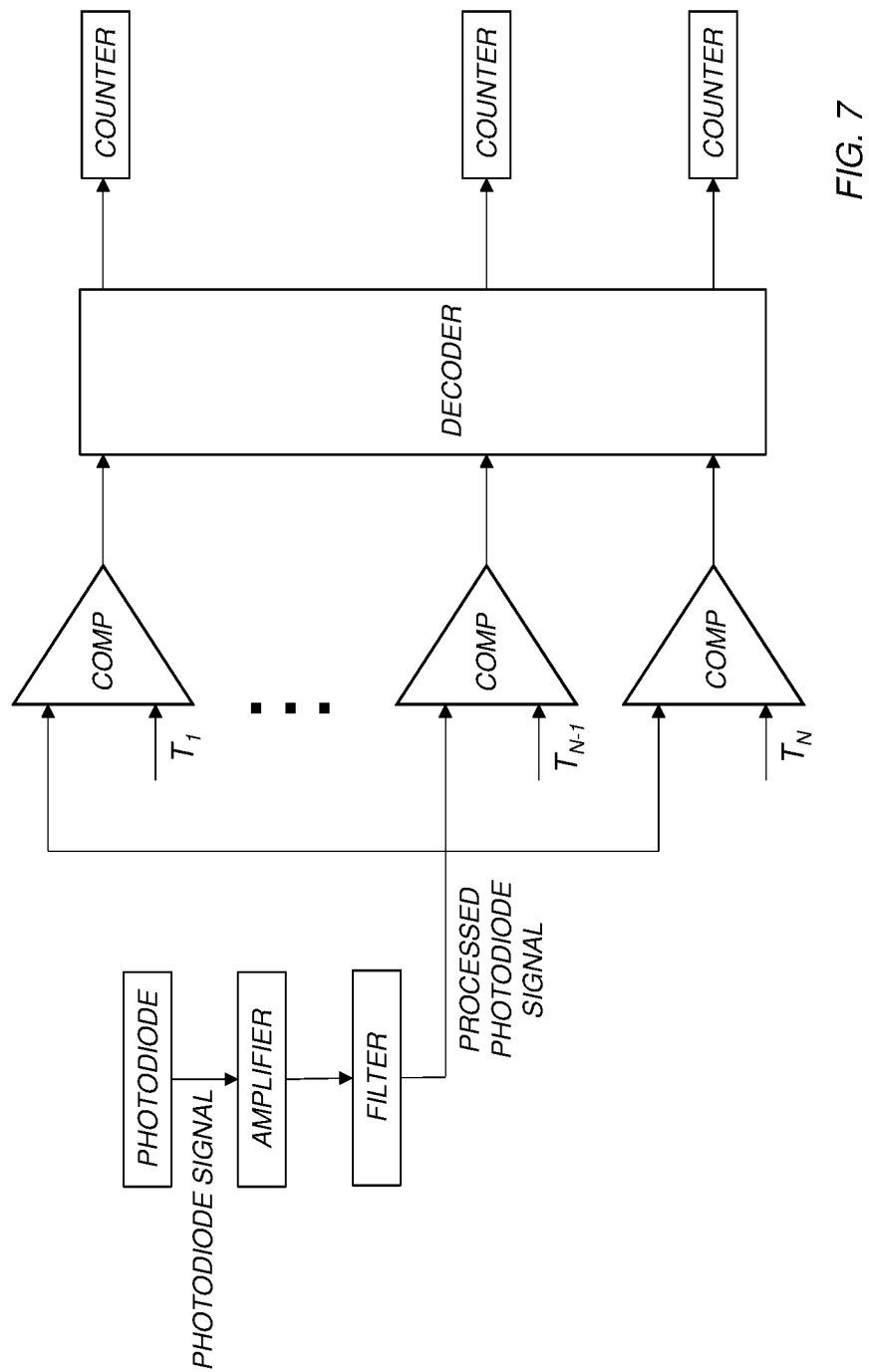
FIG. 7 is a schematic diagram of a photon-counting detector with several energy thresholds.

In general, the X-ray photons, including also photons after Compton scattering, are converted to electron-hole pairs inside the semiconductor substrate of the detector modules, where the number of electron-hole pairs is generally proportional to the photon energy. The electrons and holes are drifting towards the detector elements, then leaving the photon-counting detector. During this drift, the electrons and holes induce an electrical current in the detector elements, a current which may be measured, e.g., through a CSA, followed by a shaping filter (SF), as schematically illustrated in FIG. 7.

As the number of electrons and holes from one X-ray event is proportional to the X-ray energy, the total charge in one induced current pulse is proportional to this energy. The current pulse is amplified in the CSA and then filtered by the SF filter. By choosing an appropriate shaping time of the SF filter, the pulse amplitude after filtering is proportional to the total charge in the current pulse, and therefore proportional to the X-ray energy. Following the SF filter, the pulse amplitude is measured by comparing its value with one or several threshold values ($T_1$-$T_N$) in one or more comparators (COMP), and counters are introduced by which the number of cases when a pulse is larger than the threshold value may be recorded. In this way it is possible to count and/or record the number of X-ray photons with an energy exceeding an energy corresponding to respective threshold value ($T_1$-$T_N$) which has been detected within a certain time frame.

When using several different threshold values, a so-called energy-discriminating photon-counting detector is obtained, in which the detected photons can be sorted into energy bins corresponding to the various threshold values. Sometimes, this type of photon-counting detector is also referred to as a multi-bin detector.

In general, the energy information allows for new kinds of images to be created, where new information is available and image artifacts inherent to conventional technology can be removed.

In other words, for an energy-discriminating photon-counting detector, the pulse heights are compared to a number of programmable thresholds ($T_1$-$T_N$) in the comparators and classified according to pulse-height, which in turn is proportional to energy.

However, an inherent problem in any CSA is that it will add electronic noise to the detected current. In order to avoid detecting noise instead of real X-ray photons, it is therefore important to set the lowest threshold value high enough so that the number of times the noise value exceeds the threshold value is low enough not to disturb the detection of X-ray photons.

By setting the lowest threshold above the noise floor, electronic noise, which is the major obstacle in the reduction of radiation dose of the X-ray imaging systems, can be significantly reduced.

Furthermore, the noise added by the CSA is dependent on the CSA current as illustrated in FIG. 11.

The shaping filter has the general property that large values of the shaping time will lead to a long pulse caused by the X-ray photon and reduce the noise amplitude after the filter. Small values of the shaping time will lead to a short pulse and a larger noise amplitude. Therefore, in order to count as many X-ray photons as possible, a large shaping time is desired to minimize noise and allowing the use of a relatively small threshold level.

The values of the set or table of thresholds, by which the pulse heights are compared in the comparators, affect the quality of the image data generated by the photon-counting detector.

In an embodiment, each power-consuming circuitry comprises multiple comparators configured to compare a current pulse generated in response to detection of a photon with a set of thresholds, see FIG. 7.

An aspect of the embodiments relates to an X-ray detector system. The X-ray detector system comprises a photon-counting detector according to the embodiments. The X-ray detector system also comprises a detector controller, see FIG. 2, connected to the photon-counting detector. In an embodiment, the detector controller is configured to select an operational mode for detector modules in the at least one second subset based on a control signal. The detector controller is also configured, in this embodiment, to control the detector modules in the at least one second subset to operate in the selected operational mode in which the power-consuming circuitry of the detector modules in the at least one second subset is configured to consume an amount of power that is lower than an amount of power consumed by the power-consuming circuitry of detector modules in the first subset.

Hence, in this embodiment, the detector modules in the at least one second subset can be run according to multiple, i.e., at least two, operational modes with regard to the power consumption of the power-consuming circuitry of the detector modules. For instance, in a first operational mode the power-consuming circuitry of the detector modules in the at least one second subset consumes a given amount of power, whereas in a second operational mode the power-consuming circuitry instead consumes another amount of power, different from the given amount of power.

In a first embodiment, there are Q different operational modes, in which the power-consuming circuitry of the detector modules in the at least second subset consumes $P_q$ W of power, wherein q=1 . . . Q. For instance, Q=2 and in the first operational mode the power-consuming circuitry consumes the first amount of power $P_1$, i.e., the same amount of power as the power-consuming circuitry of the detector modules in the first subset. However, in the second operational mode the power-consuming circuitry consumes the second amount of power $P_2<P_1$. Thus, the second operational mode could be regarded as a low-power consuming operational mode, whereas the first operational mode is the normal or default operational mode. In an alternative example, the power-consuming circuitry of the detector modules in the at least one second subset consumes $P_1$ and $P_2$ amount of power in the first and second operational modes, respectively, whereas the power-consuming circuitry of the detector modules in the first subset consumes $P_n$ amount of power, in which $P_2<P_1<P_n$. Hence, both the first and second operational modes are low-power consuming operational modes as compared to the operational mode of the detector modules in the first subset.

This concept can of course be applied to the situation with more than two different operational modes for the detector modules in the at least one second subset.

In the above described embodiments, there is a set of multiple defined operational modes with defined power levels. This means that the amount of power consumed by the power-consuming circuitry of the detector modules in the at least one second subset can be changed in discrete steps by the detector controller.

In an alternative embodiment, the detector controller can vary the power consumption of the power-consuming circuitry of the detector modules in the at least one second subset more or less continuously, i.e., not necessarily in predefined steps.

In an embodiment, each power-consuming circuitry is a respective ASIC and each ASIC comprises at least one respective input channel connected to a respective detector element in the detector module. Each such input channel comprises a respective amplifier, such as CSA, as shown in FIG. 7. In such an embodiment, the detector controller is configured to set a current input to the respective amplifier, such as CSA, in the ASICs of the detector modules in the at least one second subset at a current level that is lower than a current level of a current input to the respective amplifier, such as CSA, in the ASICs of the detector modules in the first subset.

Hence, in the low-power consuming operational mode or in one of multiple available low-power consuming operational modes, the current input to the CSAs in the ASICs of the detector modules in the at least one second subset is lower than the current input to the CSAs in the ASICs of the detector modules in the first subset.

For instance, in the case of two operational modes the detector controller could be configured to set the current input to the CSAs in the ASICs of the detector modules in the at least one second subset at a current level $I_1$ or $I_2$, in which $I_2<I_1$. In first case, $I_1$ is equal to the current input to the CSAs in the ASICs of the detector modules in the first subset. In a second case, $I_n$ represents the current input to the CSAs in the ASICs of the detector modules in the first subset and $I_2<I_1<I_n$.

In an embodiment, the detector controller is configured to set the current according to one among multiple defined current levels, i.e., stepwise changing the current input to the CSAs in the ASICs of the detector modules in the at least one second subset. In another embodiment, the detector controller is configured to vary the current continuously between a minimum level, such as zero, and a maximum level, such as $I_n$.

In an embodiment, each power-consuming circuitry is a respective ASIC and each ASIC comprises multiple input channels connected to a respective detector element in the detector module. Each input channel comprises a respective amplifier, preferably a respective CSA. In such an embodiment, the detector controller is configured to set a respective current input to the respective amplifier, preferably CSA, in the ASICs of the detector modules in the at least one second subset so that a total current consumption of the respective amplifier, preferably CSA, in the ASICs of the detector modules in the at least one second subset is lower than a total current consumption of the respective amplifier, preferably CSA, in the ASICs of the detector modules in the first subset.

As mentioned in the foregoing, the detector controller is configured to select the operational mode based on a control signal. In an embodiment, the control signal is generated by a user input device, represented by the operator console in FIG. 2. The user input device could, for instance, be in the form of a keyboard, a mouse, a touch-sensitive screen, etc., which is used by the user or operator to select an operational mode for the detector modules in the at least one second subset. Thus, activating the user input device, such as by pressing a key, clicking on the mouse or touching a designated area of the touch-sensitive screen, generates the control signal. The user thereby manually selects which operational mode to use for the current subject.

In an embodiment, the photon-counting detector can be operated according to multiple imaging modes. Each such imaging mode is then adapted to at least one respective organ or tissue to be imaged by the photon-counting detector. In such a case, the detector controller is configured to select the operation mode based on a control signal representing an imaging mode among the multiple imaging modes.

For instance, a heart imaging mode is used when imaging the heart of the subject, a brain imaging mode is used when imaging the brain of the subject, etc. A full body imaging mode could be used when imaging the full body or at least a major portion thereof. Correspondingly, a torso imaging mode could be used when imaging the torso of the subject.

In such a case, the amount of power consumed by the power-consuming circuitry of the detector modules in the at least one second subset, such as the current input to the CSAs of the ASICs in these detector modules, is determined or set by the detector controller based on the selected imaging mode. For instance, in the case of a full body scan or imaging a larger portion of the body, such as in the full body or torso imaging mode, all detector modules of the photon-counting detector might be needed to operate at full, nominal power in order to, for instance, detect trauma or damages somewhere in the body or torso. Thus, the interesting part to be imaged might not necessarily be in or even close to the isocenter. In this case, it is important to achieve sufficient image quality also in the peripheral parts of the image. This should be compared to an imaging mode in which the target organ or tissue to image is comparatively small and centered at or close to the isocenter. In such a case, the image quality in the peripheral parts of the image is less important. Accordingly, the power consumption of the power-consuming circuitry of the detector modules in the at least one second subset could then be reduced significantly as compared to the power consumption in the detector modules in the first subset.

In an embodiment, the X-ray detector system comprises at least one temperature sensor configured to monitor a temperature of the photon-counting detector and generate the control signal representing a temperature of the photon-counting detector.

FIG. 6 illustrates one exemplary arrangement of a temperature sensor in a detector module, such as in the ASIC of the detector module. For instance, each detector module could comprise a respective temperature sensor arranged, for instance, in one ASIC or indeed a temperature sensor in each ASICs in the detector modules. Alternatively, temperature sensors could be arranged in only a selection portion of the detector modules. Furthermore, one or more temperature sensors may alternatively, or in addition, be arranged elsewhere in the photon-counting detector in order to monitor the temperature of the photon-counting detector.

In an embodiment, the control signal generated by the temperature sensor is representative of a current temperature on the photon-counting detector as determined based on the temperature monitoring. In an embodiment, each temperature sensor is integrated in a respective power-consuming circuitry of at least a subset of the detector modules as shown in FIG. 6. In such a case, each power-consuming circuitry, represented by ASIC in the figure, could comprises a respective temperature sensor. Alternatively, only a subset of the power-consuming circuitries, such as ASICs, per detector module comprises a respective temperature sensor. For instance, only one ASIC per detector module could comprise a temperature sensor.

It is also possible to have the temperature sensor(s) arranged elsewhere on the detector modules than integrated in the power-consuming circuitries. For instance, the temperature sensor could be arranged on the semiconductor substrate.

In an embodiment, each temperature sensor is an oscillator-based temperature sensor configured to measure a frequency change in an oscillator implemented in a respective power-consuming circuitry of the at least a subset of the multiple detector modules. Such an implementation of a temperature sensor is in particular suitable for integration in an ASIC.

If the photon-counting detector comprises multiple temperature sensors the control signal could represent the average temperature of the photon-counting sensor. In an alternative embodiment, the control signal represents the (average) temperature of the detector modules in the at least one second subset or the (average) temperature of the detector modules in the first subset.

In this embodiment, the amount of power to be consumed by the power-consuming circuitry of the detector modules in the at least one second subset is selected by the detector controller based on the temperature of the photon-counting detector as represented by the control signal from the temperature sensor.

For instance, the detector controller could be configured to use as high power for the detector modules in the at least one second subset as long as the temperature of the photon-counting detector is within a given temperature range or below a given temperature. However, if the temperature of the photon-counting detector starts to increase as represented by the control signal the detector controller could reduce the power to the detector modules in the at least one second subset to thereby reduce the total power consumption of the photon-counting detector and thereby reduce or at least control the temperature of the photon-counting detector.

In an embodiment, the detector controller is configured to select detector modules belonging to the at least one second subset and/or select detector modules belonging to the first subset based on a selection signal.

Hence, in this embodiment the number of detector modules in the first subset and in the at least one second subset is not fixed but can rather change based on the selection signal. This means that a given detector module may in some applications be selected by the detector controller to belong to the first subset, whereas in other applications the detector module is selected to belong to the at least one second subset.

In an embodiment, the selection signal is generated by a user input device, similar to what has been described in the foregoing in connection with the control signal. In this embodiment, the user may thereby select the size of the respective subsets of the detector modules in the photon-counting detector using the user input device. For instance, the user could use the user input device to mark, on a screen, the detector modules in the photon-counting detector that should belong to the first subset and/or belong to the at least one second subset.

In a particular embodiment, the photon-counting detector comprises the first subset of detector modules, whereas the remaining detector modules in the photon-counting detector belongs to the at least one second subset. Hence, it is sufficient to define the detector modules that belong to the first (or second) subset, since remaining detector modules will then belong to the second (or first) subset.

In an embodiment, the detector controller is configured to select detector modules belonging to the at least one second subset and/or select detector modules belonging to the first subset based on the selection signal representing an image mode among multiple imaging modes for the photon-counting detector.

For instance, if the photon-counting detector is to be used to image a spatially limited organ or tissue, such as the heart, centered or at least close to the isocenter, the heart imaging mode can be selected. In such a case, the detector controller is configured to select the detector modules belonging to the first and/or at least one second subset based on the selection signal indicating the heart imaging mode. Hence, in this mode it may be sufficient that the first subset contains only a limited central subset of detector modules in the photon-counting detector, whereas peripheral detector modules should then belong to the second subsets. Thus, the number of detector modules in the central subset could thereby be determined and selected by the detector controller based on the imaging mode and thereby the size of the organ or tissue to imaged. Generally, the larger the organ or tissue the more detector modules in the central (first) subset and thereby fewer detector modules in the peripheral (second) subsets.

The above described embodiments of selecting detector modules for the first and second subsets based on the selection signal can be combined with selecting operational mode based on the control signal. Alternatively, the selection of detector modules can be used independent from selecting operational mode. In this latter case the X-ray detector system comprises a photon-counting detector according to the embodiments. The X-ray detector system also comprises a detector controller connected to the photon-counting detector and configured to select detector modules of the photon-counting detector belonging to the at least one second subset and/or select detector modules of the photon-counting detector belonging to the first subset based on a selection signal. The detector controller is also configured to control the detector modules in the at least one second subset to operate in an operational mode in which the power-consuming circuitry of the detector modules in the at least one second subset is configured to consume an amount of power that is lower than an amount of power consumed by power-consuming circuitry of the detector modules in the first subset.

In a particular embodiment, the detector controller of the X-ray detector system is connected to the photon-counting detector and is configured to selectively switch detector modules in the at least one second subset between a second power consumption operational mode in which the power-consuming circuitry of the detector modules is configured to consume the second amount of power and a first power consumption operational mode in which the power-consuming circuitry of the detector modules is configured to consume the first amount of power or an amount of power larger than the second amount of power but lower than the first amount of power.

Hence, in this embodiment, the detector controller can switch the power consumption of the power-consuming circuitry of the detector modules in the at least one second subset between different power consumption operational modes. In the second, or low-power consumption operational mode, the power-consuming circuitry consumes the second amount of power. In the first, or high-power consumption operational mode, the power-consuming circuitry consumes the same amount of power as the power-consuming circuitry of the detector modules in the first subset, i.e., the first amount of power, or an amount of power larger than the second amount of power but still lower than the first amount of power.

In a particular embodiment, the detector controller is configured to switch the input current to amplifiers, such as CSAs, in the ASICs of the detector modules to achieve different levels of power consumption as disclosed herein.

As mentioned in the foregoing, the detector modules in the at least one second subset could be controlled to consume a varying amount of power or be switched between different predefined levels of power consumption. In these embodiments, the detector modules in the at least one second subset are preferably identical to the detector modules in the first subset but with the difference that they may be operated at reduced power consumption. However, the power-consuming circuitries, i.e., ASICs, and depth elements of the detector modules may be identical regardless of belonging to the first or second subset.

In another embodiment, the detector modules in the at least one second subset are different from the detector modules in the first subset. For instance, since the most interesting image features are often located near the isocenter, the highest spatial resolution should be in the central parts of the image. This can be achieved by having smaller pixels near the isocenter. Smaller pixels adds most information to the image if they are at the center of the photon-counting detector for most imaging tasks. Smaller pixels is a driver of data rate and power and normally there is a constraint on total power and data rate that a photon-counting detector can handle in order to be practical. Too much power would put the photon-counting detector at too high temperature or ambient temperature in the room will be uncomfortably high or it will require expensive cooling system installations, such as water cooling instead of air cooling.

It is, thus, possible to vary the spatial resolution in such a way that the spatial resolution in the center, i.e., first subset of detector modules, is higher than in the periphery, i.e., the second subsets of detector modules. Accordingly, the detector modules in the first subset may have smaller pixels as compared to the detector modules in the at least one second subset.

Figure 13:
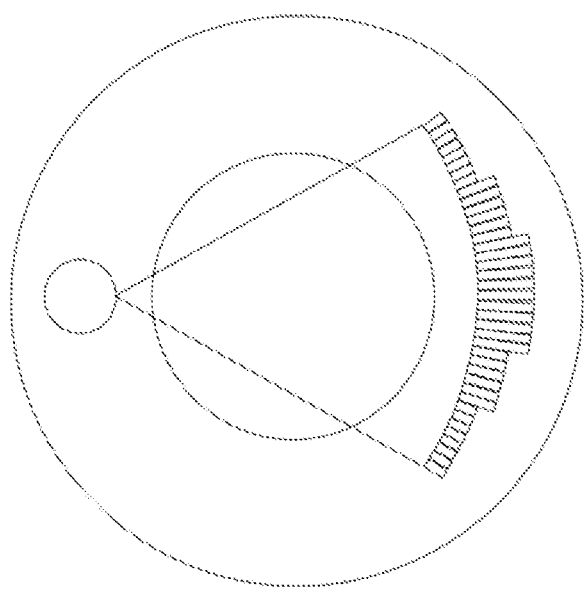
FIG. 13 is a schematic diagram of a photon-counting detector according to another embodiment.
Figure 12:
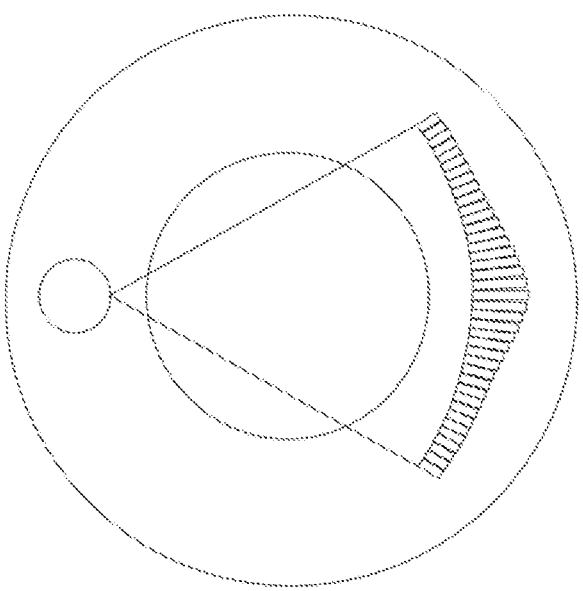
FIG. 12 is a schematic diagram of a photon-counting detector according to an embodiment.

Smaller pixels can be achieved by means of smaller detector elements and/or more depth segments in the detector modules. For instance, the detector modules in the first subset may have larger thickness as compared to detector modules in the at least one second subset. This is schematically illustrated in FIGS. 12 and 13. In FIG. 12, the detector module thickness is largest at the center and then decreases gradually towards the peripheral ends of the photon-counting detector. In FIG. 13, the detector module thickness instead changes in steps for the center towards the peripheral ends.

In the foregoing, the photon-counting detector has mainly been described with reference to a first subset of detector modules and at least one second subset of detector modules. This concept can of course be extended to the case of more than two different subset of detector modules. For instance, there could be a central subset of detector modules, intermediate subsets of detector modules and peripheral subsets of detector modules as schematically illustrated in FIG. 13. In such a case, the power consumption of detector modules could be different in the three different types of subsets, such as higher power consumption in the central subset, intermediate power consumption in the intermediate subsets and lower power consumption in the peripheral subsets.

Figure 8:
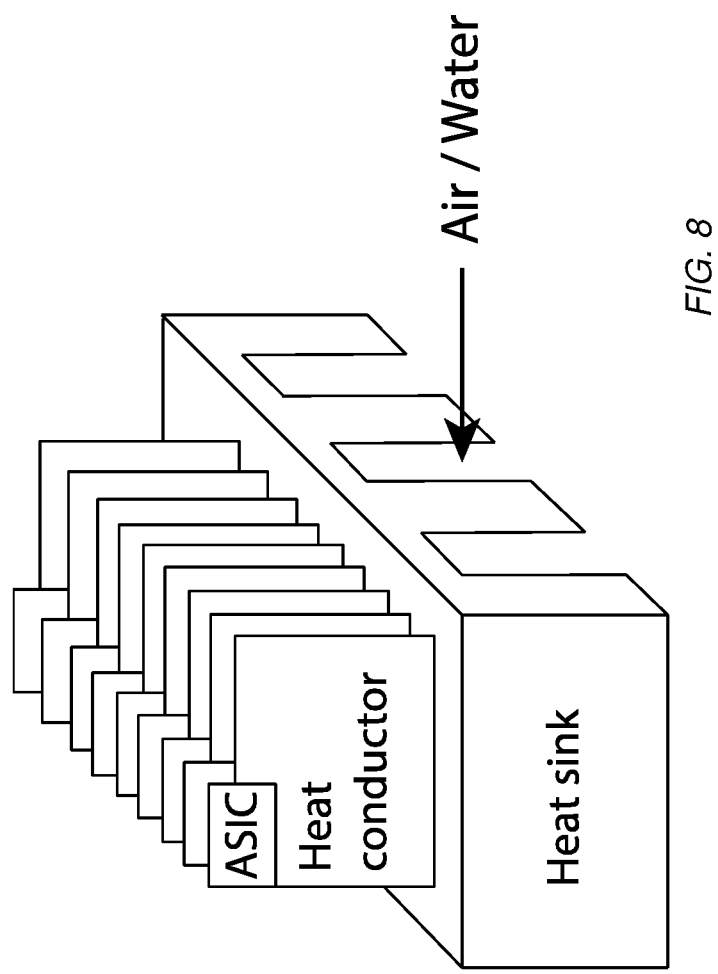
FIG. 8 is a schematic diagram of heat dissipation of a photon-counting detector according to an embodiment.

In an embodiment, the photon-counting detector is connected with a heat conductor from the front-end ASIC to a heat sink as illustrated in FIG. 8. The heat conductor is, in an embodiment, made of aluminum nitride since its temperature expansion coefficient is matched to silicon. In an embodiment, the heat sink is made of aluminum due to its comparatively low density, thereby reducing the weight of the heat sink. Ambient air or water can be used to take away the heat from the heat sink.

Hence, in an embodiment, the photon-counting detector comprises a heat sink and multiple heat conductors. Each heat conductor interconnects a power-consuming circuitry of a detector module and the heat sink.

In an embodiment, the multiple heat conducts are made of aluminum nitride. In an embodiment, the heat sink is made of aluminum.

Figure 10:
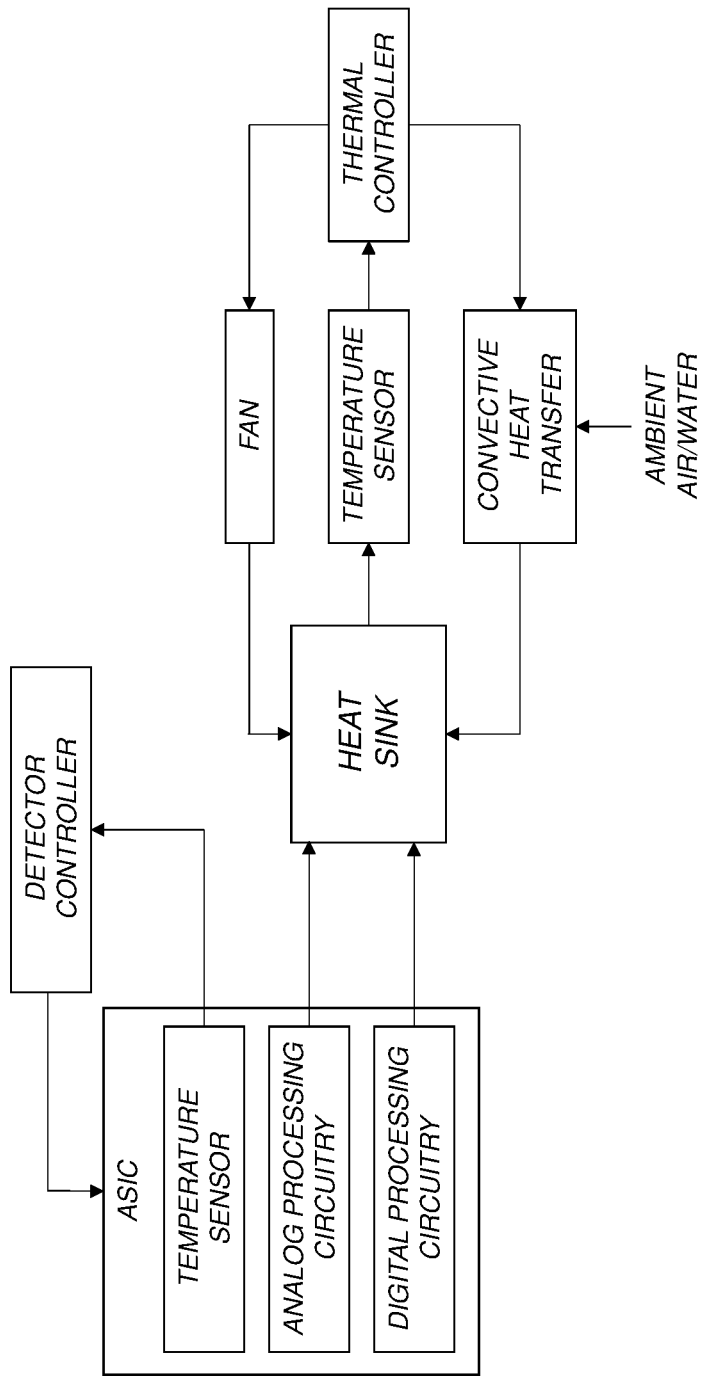
FIG. 10 is a schematic block diagram of thermal management of a photon-counting detector according to an embodiment.

A simplified model for the thermal management system of the photon-counting detector is shown in FIG. 10. In an embodiment, the thermal management system may comprise a heat sink as mentioned in the foregoing. After the X-ray imaging system has been turned on, the power-consuming circuitries, represented by analog and digital processing circuitries in the figure generate heat that is delivered to the heat sink. Convective heat transfer and a fan of the thermal management system help to spread the heat out from the photon-counting detector and the heat sink and thereby keep the photon-counting detector at a generally constant temperature. The operation of the fan and/or convective heat transfer may be operated by a thermal controller, see also FIG. 2, in response to temperature signals from one or more temperature sensors.

Figure 9:
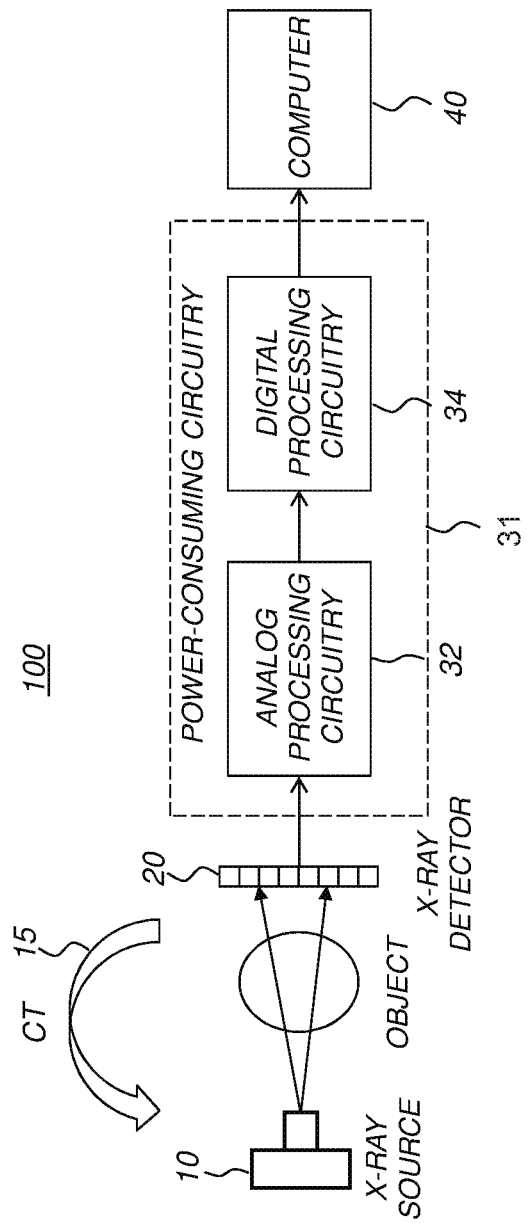
FIG. 9 is a schematic block diagram of an X-ray imaging system according to a further embodiment.

As illustrated in FIG. 9, another example of an X-ray imaging system 100 comprises an X-ray source 10, which emits x-rays; an X-ray detector system 20, which detects the X-rays after they have passed through the object; a power-consuming circuitry 31, such as ASIC, integrated in the detector modules of the photon-counting detector. In an embodiment, the power-consuming circuitry 31 comprising analog processing circuitry 32, which processes the raw electrical signal from the detector elements and digitizes it, and digital processing circuitry 34 which may carry out further processing operations on the measured data, such as applying corrections, storing it temporarily, or filtering. The X-ray imaging system 100 also comprises a computer 40, which stores the processed data and may perform further post-processing and/or image reconstruction.

An example of a commonly used X-ray imaging system is a CT system, which may include an X-ray source 10 that produces a fan or cone beam of X-rays and an opposing X-ray detector system 20 for registering the fraction of X-rays that are transmitted through a patient or object. The X-ray source 10 and photon-counting detector are normally mounted in a gantry that rotates around the imaged object as indicated by the arrow 15.

Thus, in an embodiment each power-consuming circuitry comprises analog processing circuitry and digital processing circuitry. In an embodiment, the power consumption of the analog processing circuitry 32 of the detector modules in the at least second subset is lower than the power consumption of the analog processing circuitry 32 of the detector modules in the first subset. In another embodiment, the power consumption of the digital processing circuitry 34 of the detector modules in the at least second subset is lower than the power consumption of the digital processing circuitry 34 of the detector modules in the first subset. In a further embodiment, the power consumption of the analog processing circuitry 32 of the detector modules in the at least second subset is lower than the power consumption of the analog processing circuitry 32 of the detector modules in the first subset and the power consumption of the digital processing circuitry 34 of the detector modules in the at least second subset is lower than the power consumption of the digital processing circuitry 34 of the detector modules in the first subset.

A further aspect of the embodiments relates to an X-ray imaging system comprising a photon-counting detector according to the embodiments or an X-ray detector system according to the embodiments.

In an embodiment, the X-ray imaging system is a CT system.

Figure 16:
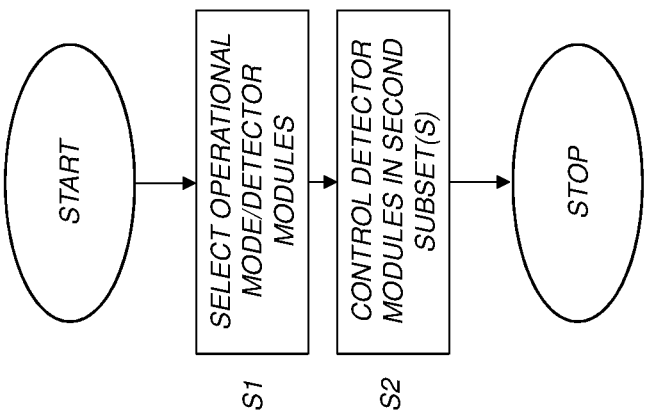
FIG. 16 is a flow chart illustrating a method of controlling of a photon-counting detector according to an embodiment.

FIG. 16 is a flow chart illustrating a method of controlling a photon-counting detector according to an embodiment. The method comprises selecting, in step S1 and based on a control signal, an operational mode for detector modules in at least one second subset of detector modules in the photon-counting detector comprising a first subset of detector modules and the at least one second subset of detector modules. Each detector module has power-consuming circuitry. The method also comprises controlling, in step S2, the detector modules in the at least one second subset to operate in the selected operational mode in which power-consuming circuitry of the detector modules in the at least one second subset is configured to consume an amount of power that is lower than an amount of power consumed by power-consuming circuitry of the detector modules in the first subset.

In another embodiment, the method of FIG. 16 comprises selecting, in step S1 and based on a selection signal, detector modules of the photon-counting detector belonging to at least one second subset of detector modules and/or selecting, based on the selection signal, detector modules of the photon-counting detector belonging to a first subset of detector modules. Each detector module has power-consuming circuitry. The method also comprises controlling, in step S2, the detector modules in the at least one second subset to operate in an operational mode in which power-consuming circuitry of the detector modules in the at least one second subset is configured to consume an amount of power that is lower than an amount of power consumed by power-consuming circuitry of the detector modules in the first subset.

The two embodiments described above in connection with FIG. 16 can be combined.

It will be appreciated that the methods, devices and arrangements described herein can be implemented, combined and re-arranged in a variety of ways.

For example, embodiments may be implemented in hardware, or in software for execution by suitable processing circuitry, or a combination thereof.

The steps, functions, procedures, modules and/or blocks described herein may be implemented in hardware using any conventional technology, such as discrete circuit or integrated circuit technology, including both general-purpose electronic circuitry and application-specific circuitry.

Alternatively, or as a complement, at least some of the steps, functions, procedures, modules and/or blocks described herein may be implemented in software such as a computer program for execution by suitable processing circuitry such as one or more processors or processing units.

Examples of processing circuitry includes, but is not limited to, one or more microprocessors, one or more Digital Signal Processors (DSPs), one or more Central Processing Units (CPUs), video acceleration hardware, and/or any suitable programmable logic circuitry such as one or more Field Programmable Gate Arrays (FPGAs), or one or more Programmable Logic Controllers (PLCs).

It should also be understood that it may be possible to re-use the general processing capabilities of any conventional device or unit in which the proposed technology is implemented. It may also be possible to re-use existing software, e.g. by reprogramming of the existing software or by adding new software components.

For instance, the detector controller of the X-ray detector system can be in the form of a processor-memory implementation according to an embodiment. In this particular example, the detector controller comprises a processor and a memory. The memory comprises instructions executable by the processor, whereby the processor is configured to selectively switch the detector modules between the idle and operational modes.

In another embodiment, the detector controller can be in the form of a hardware circuitry implementation according to an embodiment. Particular examples of suitable hardware circuitry include one or more suitably configured or possibly reconfigurable electronic circuitry, e.g. Application Specific Integrated Circuits (ASICs), Field Programmable Gate Arrays (FPGAs), or any other hardware logic such as circuits based on discrete logic gates and/or flip-flops interconnected to perform specialized functions in connection with suitable registers (REG) and/or memory units (MEM).

It is also possible to provide a solution based on a combination of hardware and software. The actual hardware-software partitioning can be decided by a system designer based on a number of factors including processing speed, cost of implementation and other requirements.

Figure 15:
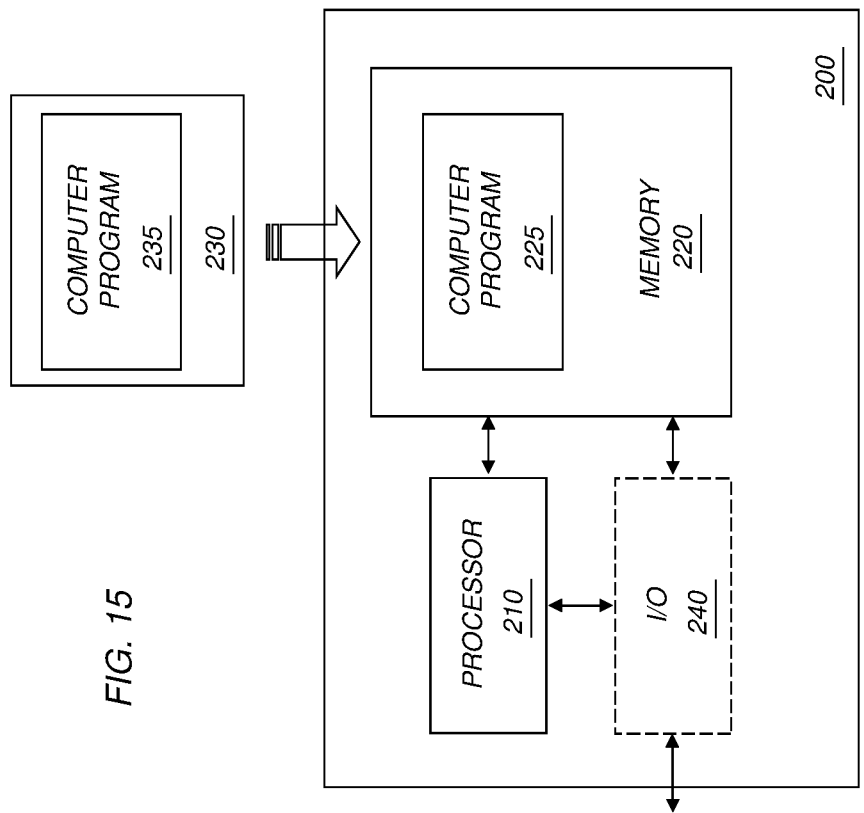
FIG. 15 is a schematic block diagram illustrating an example of computer implementation according to an embodiment.

FIG. 15 is a schematic diagram illustrating an example of a computer-implementation 200 according to an embodiment. In this particular example, at least some of the steps, functions, procedures, modules and/or blocks described herein are implemented in a computer program 225; 235, which is loaded into the memory 220 for execution by processing circuitry including one or more processors 210. The processor(s) 210 and memory 220 are interconnected to each other to enable normal software execution. An optional input/output device 240 may also be interconnected to the processor(s) 210 and/or the memory 220 to enable input and/or output of relevant data such as input parameter(s) and/or resulting output parameter(s).

The term 'processor' should be interpreted in a general sense as any system or device capable of executing program code or computer program instructions to perform a particular processing, determining or computing task.

The processing circuitry including one or more processors 210 is thus configured to perform, when executing the computer program 225, well-defined processing tasks such as those described herein.

The processing circuitry does not have to be dedicated to only execute the above-described steps, functions, procedure and/or blocks, but may also execute other tasks.

The proposed technology also provides a computer program 225; 235 comprising instructions, which when executed by at least one processor 210, cause the at least one processor 210 to select, based on a control signal, an operational mode for detector modules in at least one second subset of detector modules in a photon-counting detector comprising a first subset of detector modules and the at least one second subset of detector modules. Each detector module has power-consuming circuitry. The at least one processor 210 is also caused to control the detector modules in the at least one second subset to operate in the selected operational mode in which power-consuming circuitry of the detector modules in the at least one second subset is configured to consume an amount of power that is lower than an amount of power consumed by power-consuming circuitry of the detector modules in the first subset.

In another embodiment, the computer program 225; 235 comprises instructions, which when executed by at least one processor 210, cause the at least one processor 210 to select, based on a selection signal, detector modules of a photon-counting detector belonging to at least one second subset of detector modules and/or select, based on the selection signal, detector modules of the photon-counting detector belonging to a first subset of detector modules. Each detector module has power-consuming circuitry. The at least one processor 210 is also caused to control the detector modules in the at least one second subset to operate in an operational mode in which power-consuming circuitry of the detector modules in the at least one second subset is configured to consume an amount of power that is lower than an amount of power consumed by power-consuming circuitry of the detector modules in the first subset.

The proposed technology also provides a computer-readable medium 230 comprising the computer program 235. The computer-readable medium 230 is one of an electronic signal, an optical signal, an electromagnetic signal, a magnetic signal, an electric signal, a radio signal, a microwave signal, or a computer-readable storage medium.

By way of example, the software or computer program 225; 235 may be realized as a computer program product, which is normally carried or stored on a computer-readable medium 230, in particular a non-volatile medium. The computer-readable medium may include one or more removable or non-removable memory devices including, but not limited to a Read-Only Memory (ROM), a Random Access Memory (RAM), a Compact Disc (CD), a Digital Versatile Disc (DVD), a Blu-ray disc, a Universal Serial Bus (USB) memory, a Hard Disk Drive (HDD) storage device, a flash memory, a magnetic tape, or any other conventional memory device. The computer program 225; 235 may thus be loaded into the memory 220 of a computer-implementation 200 (which may be a computer or equivalent processing device) for execution by the processing circuitry 210 thereof.

The flow diagram or diagrams presented herein may be regarded as a computer flow diagram or diagrams, when performed by one or more processors. A corresponding device may be defined as a group of function modules, where each step performed by the processor corresponds to a function module. In this case, the function modules are implemented as a computer program running on the processor.

The computer program residing in memory may thus be organized as appropriate function modules configured to perform, when executed by the processor, at least part of the steps and/or tasks described herein.

In an embodiment, such a device comprises a selecting module for selecting, based on a control signal, an operational mode for detector modules in at least one second subset of detector modules in a photon-counting detector comprising a first subset of detector modules and the at least one second subset of detector modules. Each detector module has power-consuming circuitry. The device also comprises a controlling module for controlling the detector modules in the at least one second subset to operate in the selected operational mode in which power-consuming circuitry of the detector modules in the at least one second subset is configured to consume an amount of power that is lower than an amount of power consumed by power-consuming circuitry of the detector modules in the first subset.

In another embodiment, such a device comprises a selecting module for selecting, based on a selection signal, detector modules of a photon-counting detector belonging to at least one second subset of detector modules and/or selecting, based on the selection signal, detector modules of the photon-counting detector belonging to a first subset of detector modules. Each detector module has power-consuming circuitry. The device also comprises a controlling module for controlling the detector modules in the at least one second subset to operate in an operational mode in which power-consuming circuitry of the detector modules in the at least one second subset is configured to consume an amount of power that is lower than an amount of power consumed by power-consuming circuitry of the detector modules in the first subset.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] U.S. Pat. No. 7,065,173
[2] U.S. Pat. No. 6,931,092
[3] U.S. Pat. No. 7,236,562
[4] U.S. Patent Application No. 2016/0174920
[5] U.S. Pat. No. 9,086,360
[6] Alvarez and Macovski. Energy-selective reconstructions in X-ray computerised tomography. Phys. Med. Biol., 21(5):733, 1976.
[7] Roessl and Proksa. K-edge imaging in X-ray computed tomography using multi-bin photon counting detectors. Phys. Med. Biol., 52(15):4679, 2007.
[8] Liu, Gronberg, Sjölin, Karlsson and Danielsson, "Count rate performance of a silicon-strip detector for photon-counting spectral CT", Nucl. Instr. and Meth. A, Volume 827, p. 102-106. 2016.
[9] Gustaysson, Amin, Bjorklid, Ehliar, Xu and Svensson. A high-rate energy-resolving photon-counting ASIC for spectral computed tomography. IEEE Transactions on Nuclear Science, 59(1), 30-39, 2012.

The invention claimed is:

1. A photon-counting detector comprising:
   a first subset of detector modules; and
   at least one second subset of detector modules, wherein,
   each detector module has power-consuming circuitry comprising analog processing circuitry and digital processing circuitry, the analog processing circuitry of detector modules in said first subset is configured, in an operational mode in which said detector modules are powered on, to consume a first non-zero amount of power, and
   the analog processing circuitry of detector modules in said at least one second subset is configured, in said operational mode, to consume a second non-zero amount of power that is lower than said first non-zero amount of power.

2. The photon-counting detector according to claim 1, wherein,
   said first subset of detector modules is a central subset of detector modules;
   said at least one second subset of detector modules is at least one peripheral subset of detector modules arranged on a respective side of said central subset along an axis of said photon-counting detector;
   said analog processing circuitry of said detector modules in said central subset is configured, in said operational mode, to consume said first non-zero amount of power; and
   said analog processing circuitry of said detector modules in said at least one peripheral subset is configured, in said operational mode, to consume said second non-zero amount of power.

3. The photon-counting detector according to claim 2, comprising:
   a first peripheral subset of detector modules arranged on a first side of said central subset along said axis of said photon-counting detector; and
   a second peripheral subset of detector modules arranged on a second, opposite side of said central subset along said axis of said photon-counting detector.

4. The photon-counting detector according to claim 1, wherein each power-consuming circuitry is a respective application specific integrated circuit, ASIC.

5. The photon-counting detector according to claim 4, wherein
   each ASIC comprises at least one respective input channel connected to a respective detector element in said detector module;
   each input channel comprises a respective amplifier;
   said respective amplifier in said ASICs of said detector modules in said first subset is configured, in said operational mode, to consume a third non-zero amount of power; and
   said respective amplifier in said ASICs of said detector modules in said at least one second subset is configured, in said operational mode, to consume a fourth non-zero amount of power that is lower than said third non-zero amount of power.

6. The photon-counting detector according to claim 4, wherein
each ASIC comprises at least one respective input channel connected to a respective detector element in said detector module;
each input channel comprises a respective charge sensitive amplifier;
said respective charge sensitive amplifier in said ASICs of said detector modules in said first subset has a first non-zero current consumption in said operational mode; and
said respective charge sensitive amplifier in said ASICs of said detector modules in said at least one second subset has a second non-zero current consumption in said operational mode, said second non-zero current consumption is lower than said first non-zero current consumption.

7. The photon-counting detector according to claim 4, wherein
each ASIC comprises multiple input channels connected to a respective detector element in said detector module;
each input channel comprises a respective charge sensitive amplifier;
a total current consumption of said respective charge sensitive amplifiers in said ASICs of said detector modules in said at least one second subset is lower than a total current consumption of said respective charge sensitive amplifiers in said ASICs of said detector modules in said first subset.

8. The photon-counting detector according to claim 7, wherein
said first subset comprises multiple silicon detector modules; and
said at least one second subset comprises multiple silicon detector modules.

9. The photon-counting detector according to claim 1, wherein,
said photon-counting detector is a photon-counting edge-on detector and each detector module having a respective edge facing incident X-rays; and
a total area of said edges of said multiple detector modules is greater than 200 centimeters squared ($cm^2$).

10. An X-ray detector system comprising:
a photon-counting detector according to claim 1; and
a detector controller connected to said photon-counting detector and configured to
i) select an operational mode for detector modules in said at least one second subset based on a control signal; and
ii) control said detector modules in said at least one second subset to operate in said selected operational mode in which said analog processing circuitry of said detector modules in said at least one second subset is configured to consume a non-zero amount of power that is lower than a non-zero amount of power consumed by said analog processing circuitry of said detector modules in said first subset.

11. The X-ray detector system according to claim 10, wherein
each power-consuming circuitry is a respective application specific integrated circuit, ASIC;
each ASIC comprises at least one respective input channel connected to a respective detector element in said detector module;
each input channel comprises a respective amplifier; and
said detector controller is configured to set a current input to said respective amplifier in said ASICs of said detector modules in said at least one second subset at a non-zero current level that is lower than a non-zero current level of a current input to said respective amplifier in said ASICs of said detector modules in said first subset.

12. The X-ray detector system according to claim 10, wherein
each power-consuming circuitry is a respective application specific integrated circuit, ASIC;
each ASIC comprises multiple input channels connected to a respective detector element in said detector module;
each input channel comprises a respective charge sensitive amplifier; and
said detector controller is configured to set a respective current input to said respective charge sensitive amplifier in said ASICs of said detector modules in said at least one second subset so that a total current consumption of said respective charge sensitive amplifiers in said ASICs of said detector modules in said at least one second subset is lower than a total current consumption of said respective charge sensitive amplifiers in said ASICs of said detector modules in said first subset.

13. The X-ray detector system according to claim 10, wherein said detector controller is configured to select said operational mode based on said control signal generated by a user input device.

14. The X-ray detector system according to claim 10, wherein said detector controller is configured to select said operational mode based on said control signal representing an imaging mode among multiple imaging modes for said photon-counting detector, wherein each imaging mode of said multiple imaging modes is adapted to at least one respective organ or tissue to be imaged.

15. The X-ray detector system according to claim 10, further comprising at least one temperature sensor configured to monitor a temperature of said photon-counting detector and generate said control signal representing a temperature of said photon-counting detector.

16. The X-ray detector system according to claim 10, wherein said detector controller is configured to select detector modules belonging to said at least one second subset and/or select detector modules belonging to said first subset based on a selection signal.

17. The X-ray detector system according to claim 16, wherein said detector controller is configured to select detector modules belonging to said at least one second subset and/or select detector modules belonging to the said subset based on said selection signal generated by a user input device.

18. The X-ray detector system according to claim 16, wherein said detector controller is configured to select detector modules belonging to said at least one second subset and/or select detector modules belonging to the said first subset based on said selection signal representing an imaging mode among multiple imaging modes for said photon-counting detector, wherein each imaging mode of said multiple imaging modes is adapted to at least one respective organ or tissue to be imaged.

19. An X-ray detector system comprising:
a photon-counting detector according to claim 1; and
a detector controller connected to said photon-counting detector and configured to
i) select detector modules of said photon-counting detector belonging to said at least one second subset and/or select detector modules of said photon-counting detector belonging to said first subset based on a selection signal; and
ii) control said detector modules in said at least one second subset to operate in an operational mode in which said analog processing circuitry of said detector modules in said at least one second subset is configured to consume a non-zero amount of power that is lower than a non-zero amount of power consumed by said analog processing circuitry of said detector modules in said first subset.

20. The X-ray detector system according to claim 19, wherein said detector controller is configured to select detector modules belonging to said at least one second subset and/or select detector modules belonging to said first subset based on said selection signal generated by a user input device.

21. The X-ray detector system according to claim 19, wherein said detector controller is configured to select detector modules belonging to said at least one second subset and/or select detector modules belonging to the said first subset based on said selection signal representing an imaging mode among multiple imaging modes for said photon-counting detector, wherein each imaging mode of said multiple imaging modes is adapted to at least one respective organ or tissue to be imaged.

22. An X-ray imaging system comprising a photon-counting detector according to claim 1.

23. The X-ray imaging system according to claim 22, wherein said X-ray imaging system is a computed tomography, CT, system.

24. A non-transitory computer readable medium on which is stored a computer program comprising instructions, which when executed by at least one processor, cause said at least one processor to
   select, based on a control signal, an operational mode for detector modules in at least one second subset of detector modules in a photon-counting detector comprising a first subset of detector modules and said at least one second subset of detector modules, each detector module having power-consuming circuitry comprising analog processing circuitry and digital processing circuitry; and
   control said detector modules in said at least one second subset to operate in said selected operational mode in the analog processing circuitry of said detector modules in said at least one second subset is configured to consume a non-zero amount of power that is lower than a non-zero amount of power consumed by the analog processing circuitry of said detector modules in said first subset.

25. A non-transitory computer readable medium on which is stored a computer program comprising instructions, which when executed by at least one processor, cause said at least one processor to
   select, based on a selection signal, detector modules of a photon-counting detector belonging to at least one second subset of detector modules and/or select, based on said selection signal, detector modules of said photon-counting detector belonging to a first subset of detector modules, each detector module having power-consuming circuitry comprising analog processing circuitry and digital processing circuitry; and
   control said detector modules in said at least one second subset to operate in an operational mode in which the analog processing circuitry of said detector modules in said at least one second subset is configured to consume a non-zero amount of power that is lower than a non-zero amount of power consumed by the analog processing circuitry of said detector modules in the said subset.

26. A method of controlling a photon-counting detector, said method comprising:
   selecting, based on a control signal, an operational mode for detector modules in at least one second subset of detector modules in said photon-counting detector comprising a first subset of detector modules and said at least one second subset of detector modules, each detector module having power-consuming circuitry comprising analog processing circuitry and digital processing circuitry; and
   controlling said detector modules in said at least one second subset to operate in said selected operational mode in which the analog processing circuitry of said detector modules in said at least one second subset is configured to consume a non-zero amount of power that is lower than a non-zero amount of power consumed by the analog processing circuitry of said detector modules in said first subset.

27. A method of controlling a photon-counting detector, said method comprising:
   selecting, based on a selection signal, detector modules of said photon-counting detector belonging to at least one second subset of detector modules and/or selecting, based on said selection signal, detector modules of said photon-counting detector belonging to a first subset of detector modules, each detector module having power-consuming circuitry comprising analog processing circuitry and digital processing circuitry; and
   controlling said detector modules in said at least one second subset to operate in an operational mode in which the analog processing circuitry of said detector modules in said at least one second subset is configured to consume a non-zero amount of power that is lower than a non-zero amount of power consumed by the analog processing circuitry of said detector modules in said first subset.

* * * * *